US00PP32869P3

(12) United States Plant Patent
de Bont

(10) Patent No.: US PP32,869 P3
(45) Date of Patent: Mar. 2, 2021

(54) ***ECHINACEA* PLANT NAMED 'HILMOOCOUR'**

(50) Latin Name: *Echinacea purpurea*
Varietal Denomination: Hilmoocour

(71) Applicant: TAKII EUROPE B.V., De Kwakel (NL)

(72) Inventor: Diony de Bont, Alphen aan de Rijn (NL)

(73) Assignee: TAKI EUROPE B.V., De Kwakel (NL)

( * ) Notice: Subject to any disclaimer, the term of this patent is extended or adjusted under 35 U.S.C. 154(b) by 0 days.

(21) Appl. No.: 16/873,727

(22) Filed: Jun. 16, 2020

(65) Prior Publication Data

US 2021/0007261 P1 Jan. 7, 2021

Related U.S. Application Data

(60) Provisional application No. 62/921,432, filed on Jun. 17, 2019.

(51) Int. Cl.
*A01H 6/14* (2018.01)
*A01H 5/02* (2018.01)

(52) U.S. Cl.
USPC ..... Plt./428

(58) Field of Classification Search
USPC ..... Plt./428
See application file for complete search history.

(56) References Cited

PUBLICATIONS

PLUTO Plant Variety Database Sep. 19, 2020. p. 1.*

* cited by examiner

*Primary Examiner* — Annette H Para
(74) *Attorney, Agent, or Firm* — C. Anne Whealy

(57) ABSTRACT

A new and distinct cultivar of *Echinacea* plant named 'Hilmoocour', characterized by its upright to somewhat outward plant habit; moderately vigorous growth habit; freely branching habit, dense and bushy appearance; strong and healthy roots and leaves; dark green-colored leaves; freely flowering habit; strong flowering stems; large inflorescences with red purple-colored ray florets; and good garden performance.

1 Drawing Sheet

Botanical designation: *Echinacea purpurea.*
Cultivar denomination: 'HILMOOCOUR'.

CROSS-REFERENCED TO CLOSELY-RELATED APPLICATIONS

Title: Varieties of *Echinacea* Plants
Inventor/Applicant: Diony de Bont
Filed: Jun. 17, 2019
Ser. No. 62/921,432
Inventor & Applicant hereby claim the benefit of this provisional U.S. Plant Patent.

STATEMENT REGARDING PRIOR DISCLOSURES BY INVENTOR & APPLICANT

An European Community Plant Breeder's Rights application for the instant plant was filed by the Applicant, Takii Europe B.V. of De Kwakel, The Netherlands on Jul. 8, 2019, application number 2019/1659. Foreign priority is not claimed to this application.

The Inventor & Applicant assert that no publications nor advertisements relating to sales, offers for sale or public distribution occurred more than one year prior to the effective filing date of this application. Any information about the claimed plant would have been obtained from a direct or indirect disclosure from the Inventor or the Applicant. Inventor & Applicant claim a prior art exemption under 35

U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea purpurea*, and hereinafter referred to by the name 'Hilmoocour'.

The new *Echinacea* plant is a product of a planned breeding program conducted by the Inventor in De Kwakel, The Netherlands. The objective of the breeding program is to develop new strong and freely flowering *Echinacea* plants with attractive inflorescences and good garden performance.

The new *Echinacea* plant originated from an open-pollination in March, 2008 in De Kwakel, The Netherlands of a proprietary selection of *Echinacea purpurea* identified as code designation T 1236, not patented, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in De Kwakel, The Netherlands in May, 2010.

Asexual reproduction of the new *Echinacea* plant by in vitro meristem culture in a controlled environment in De Kwakel, The Netherlands since January, 2016 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilmoocour'. These characteristics in combination distinguish 'Hilmoocour' as a new and distinct *Echinacea* plant:

1. Upright to somewhat outward plant habit.
2. Moderately vigorous growth habit.
3. Freely branching habit, dense and bushy appearance.
4. Strong and healthy roots and leaves.
5. Dark green-colored leaves.
6. Freely flowering habit.
7. Strong flowering stems.
8. Large inflorescences with red purple-colored ray florets.
9. Good garden performance.

Plants of the new *Echinacea* can be compared to plants of the female parent selection. Plants of the new *Echinacea* differ from plants of the female parent selection in the following characteristics:

1. Leaves of plants of the new *Echinacea* are darker green in color than leaves of plants of the female parent selection.
2. Plants of the new *Echinacea* are more freely flowering than plants of the female parent selection.
3. Plants of the new *Echinacea* have larger inflorescences than plants of the female parent selection.
4. Ray florets of plants of the new *Echinacea* are darker red purple in color than ray florets of plants of the female parent selection.

Plants of the new *Echinacea* can be compared to plants of *Echinacea purpurea* 'Hilmoooawak', disclosed in a U.S. Plant patent application Ser. No. 14/756,665, now abandoned. In side-by-side comparisons, plants of the new *Echinacea* differ primarily from plants of 'Hilmoooawak' in the following characteristics:

1. Plants of the new *Echinacea* are more compact and have shorter peduncles than plants of 'Hilmoooawak'.
2. Plants of the new *Echinacea* are more freely flowering than plants of 'Hilmoooawak'.

BRIEF DESCRIPTION OF THE PHOTOGRAPH

The accompanying photograph illustrates the overall appearance of the new *Echinacea* plant showing the colors as true as it is reasonably possible to obtain in colored reproductions of this type. Colors in the photograph may differ slightly from the color values cited in the detailed botanical description which accurately describe the colors of the new *Echinacea* plant.

The photograph (FIG. 1) is a side perspective view of a typical flowering plant of 'Hilmoocour' grown in a container.

DETAILED BOTANICAL DESCRIPTION

The aforementioned photograph and following observations and measurements describe plants grown during the spring and summer in 15-cm containers in a glass-covered greenhouse and "finished" in an outdoor nursery in De Kwakel, The Netherlands under cultural practices typically used in commercial *Echinacea* production. During the production of the plants, greenhouse day temperatures ranged from 12° C. to 14° C., outdoor nursery day temperatures ranged from 14° C. to 20°, greenhouse night temperatures ranged from 12° to 14° and outdoor nursery night temperatures ranged from 7° C. to 15° C. Plants were 25 weeks from planting when the photograph and description were taken. In the following description, color references are made to The Royal Horticultural Society Colour Chart, 2015 Edition, except where general terms of ordinary dictionary significance are used.

Botanical classification: *Echinacea purpurea* 'Hilmoocour'.

Parentage:

*Female parent*.—Proprietary selection of *Echinacea purpurea* identified as code designation T 1236, not patented.

*Male parent*.—Unknown selection of *Echinacea purpurea*, not patented.

Propagation:

*Type*.—By in vitro meristem culture.

*Time to initiate roots, summer*.—About five weeks at temperatures about 20° C. for the first two weeks, then at temperatures about 12° C. to 14° C.

*Time to initiate roots, winter*.—About six weeks at temperatures about 20° C. for the first two weeks, then at temperatures about 14° C. to 20° C.

*Time to produce a rooted young plant, summer*.—About five weeks at temperatures about 14° C. to 20° C.

*Time to produce a rooted young plant, winter*.—About six weeks at temperatures about 18° C.

*Root description*.—Medium in thickness, fibrous; strong and healthy; typically white to brown in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous perennial; upright to somewhat outward plant habit, narrow obovate in overall shape; freely branching habit with about twelve branches developing per plant; moderately vigorous growth habit.

*Plant height*.—About 49.9 cm.

*Plant diameter or spread*.—About 34.5 cm.

*Lateral branches*.—Length: About 17.9 cm. Diameter: About 4 mm. Internode length: About 3.4 cm. Aspect: Erect to about 15° from vertical. Strength: Strong. Texture: Sparsely to moderately pubescent, strigose; rough. Color: Close to 146D strongly tinged with close to 176A to 176B.

Leaf description:

*Basal leaves*.—Arrangement: Alternate, simple. Length: About 9.7 cm. Width: About 4.6 cm. Shape: Ovate to narrowly ovate. Apex: Narrowly acute. Base: Attenuate. Margin: Coarsely and shallowly serrate; slightly to moderately undulate. Texture and luster, upper surface: Moderately pubescent, strigose; rough; slightly glossy. Texture and luster, lower surface: Moderately pubescent, strigose;

rough; matte. Venation pattern: Pinnate. Color: Developing leaves, upper surface: Close to 138A. Developing leaves, lower surface: Close to between 144A to 146B. Fully expanded leaves, upper surface: Close to NN137B; venation, close to 146C. Fully expanded leaves, lower surface: Close to between 146A and 147B; venation, close to 146D.

*Petioles, basal leaves*.—Length: About 5.8 cm. Diameter: About 3 mm by 5 mm. Strength: Strong, flexible. Texture, upper and lower surfaces: Smooth, glabrous; margins with sparse pubescence. Color, upper surface: Darker than 143A; midvein, close to 176A. Color, lower surface: Close to 147B; midvein, close to 146C.

*Cauline leaves*.—Arrangement: Alternate, simple. Length: About 8.8 cm. Width: About 3.7 cm. Shape: Narrowly ovate. Apex: Narrowly acute. Base: Attenuate. Margin: Coarsely and shallowly serrate; slightly to moderately undulate. Texture and luster, upper surface: Moderately pubescent, strigose; rough; slightly glossy. Texture and luster, lower surface: Moderately pubescent, strigose; rough; matte. Venation pattern: Pinnate. Color: Developing leaves, upper surface: Close to 138A. Developing leaves, lower surface: Close to between 144A to 146B. Fully expanded leaves, upper surface: Close to NN137B; venation, close to 146C. Fully expanded leaves, lower surface: Close to between 146A and 147B; venation, close to 146D.

*Petioles, cauline leaves*.—Length: About 2.4 cm. Diameter: About 3 mm by 5 mm. Strength: Strong, flexible. Texture, upper and lower surfaces: Smooth, glabrous; margins with sparse pubescence. Color, upper surface: Darker than 143A; midvein, close to 176A. Color, lower surface: Close to 147B; midvein, close to 146C.

Inflorescence description:

*Appearance*.—Terminal rotate single-type inflorescences with ray and disc florets arranged on a capitulum; inflorescences positioned upright above the foliar plane on mostly upright and strong peduncles.

*Flowering habit*.—Freely flowering habit with about 24 open inflorescences per plant at one time.

*Fragrance*.—None detected.

*Time to flower*.—Plants begin flowering about five to six months after planting; in the garden, plants flower continuously from early June to late September in The Netherlands.

*Inflorescence longevity*.—Inflorescences maintain good substance for about three weeks on the plant; inflorescences persistent.

*Inflorescence buds*.—Height: About 2 cm. Diameter: About 2.7 cm. Shape: Flattened globular. Color: Involucral bracts, close to N186C and 187A; immature ray florets, close to 184C.

*Inflorescence size*.—Diameter: About 10.3 cm. Depth (height): About 3.7 cm. Disc diameter: About 3.4 cm.

*Receptacles*.—Height: About 1.3 cm. Diameter: About 1.3 cm. Shape: Flattened globular. Color: Close to 155C.

*Ray florets*.—Quantity and arrangement: About 21 to 29 arranged in about two whorls at the base of the receptacle. Length: About 4.3 cm. Width: About 1.1 cm. Shape: Oblanceolate to narrowly elliptic. Apex: Deeply emarginate, praemorse. Base: Cuneate. Margin: Entire. Texture and luster, upper surface: Smooth, glabrous; slightly velvety; carinate; matte. Texture and luster, lower surface: Smooth, glabrous; carinate; matte. Aspect: Horizontal to drooping, about 20° from horizontal. Color: When opening, upper surface: Close to 64B. When opening, lower surface: Close to 186A and 187D. Fully opened, upper surface: Close to 64B; venation, close to 64B; color becoming closer to 186B with development. Fully opened, lower surface: Close to 60C; color becoming closer to 184D and 185D with development.

*Disc florets*.—Quantity and arrangement: About 400 spirally arranged at the center of the inflorescence. Length: About 1.2 cm. Diameter: About 3 mm. Shape: Lower 90% fused into a tube, apices acute; free margins, entire. Texture and luster, inner and outer surfaces: Smooth, glabrous; moderately glossy. Color, immature, inner and outer surfaces: Apex: Close to 183A. Mid-section: Close to 143C. Base: Close to 145C. Color, mature, inner and outer surfaces: Apex: Close to 185A. Mid-section and base: Close to 153D.

*Receptacle spines*.—Quantity: One per disc floret. Shape: Acicular. Apex: Narrowly acute. Base: Attenuate. Texture and luster: Smooth, glabrous; glossy. Color: Apex: Close to N34A. Mid-section: Close to 34B. Base: Close to 144C; at the base, close to 145D.

*Involucral bracts*.—Quantity and arrangement: About 80 arranged in about three whorls. Length: About 1.2 cm. Width: About 3 mm. Shape: Narrowly ovate to lanceolate. Apex: Acute. Base: Cuneate. Margin: Entire. Texture and luster, upper surface: Smooth, glabrous; slightly glossy. Texture and luster, lower surface: Smooth and mostly glabrous, margins are moderately pubescent; matte. Color, upper surface: Close to 138A. Color, lower surface: Close to 138B.

*Peduncles*.—Length: About 14.2 cm. Diameter: About 4 mm. Strength: Strong. Aspect: Upright. Texture: Moderately pubescent, strigose. Color: Close to 146A strongly tinged with close to 183A.

*Reproductive organs*.—Androecium (present on ray and disc florets): Quantity per floret: About five. Filament length: About 4 mm. Filament color: Close to 145D. Anther shape: Narrowly oblong. Anther length: About 3 mm. Anther color: Close to between 200A and 202A. Pollen amount: Scarce. Pollen color: Close to 17A. Gynoecium (present only on disc florets): Quantity per floret: One. Pistil length: About 8 mm. Stigma shape: Decurrent, unequal. Stigma color: Close to 185A. Style length: About 6 mm. Style color: Close to 150D. Ovary color: Close to 157D. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea*.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Hilmoocour' as illustrated and described.

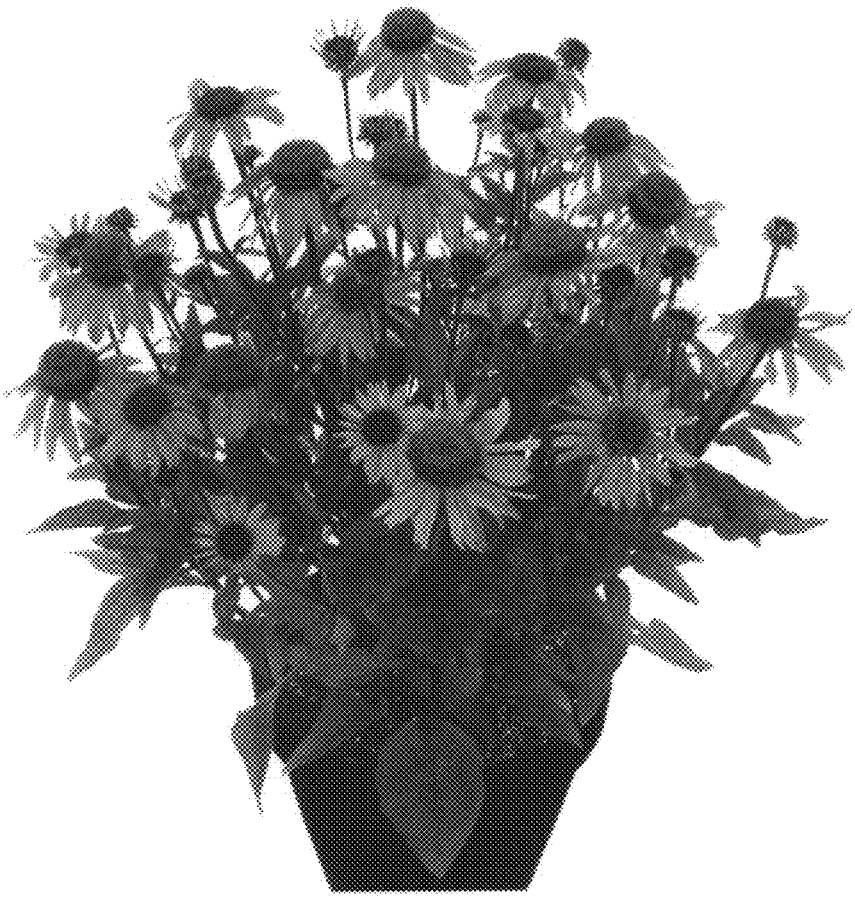

* * * * *